United States Patent [19]
Schultz et al.

[11] Patent Number: 5,814,449
[45] Date of Patent: Sep. 29, 1998

[54] HOMOGENOUS AFFINITY ASSAY FOR QUANTITATIVE DRUG AND METABOLITE DETERMINATION

[75] Inventors: Jerome S. Schultz; Ralph Ballerstadt, both of Pittsburgh, Pa.

[73] Assignee: University of Pittsburgh, Pittsburgh, Pa.

[21] Appl. No.: 653,844

[22] Filed: May 28, 1996

[51] Int. Cl.$^6$ ........................ G01N 33/53; G01N 33/543
[52] U.S. Cl. .................................. 435/6; 422/55; 422/58; 422/82.07; 422/82.08; 422/82.09; 435/7.1; 435/7.8; 435/7.93; 435/7.94; 435/7.95; 435/287.1; 435/287.2; 435/288.5; 435/288.7; 435/968; 435/808; 436/164; 436/165; 436/172; 436/536; 436/537; 436/800; 436/805; 436/518
[58] Field of Search ............................ 422/55, 58, 82.07, 422/82.08, 82.09; 435/7.1, 7.8, 7.93, 7.94, 7.95, 288.5, 295.3, 968, 6, 287.1, 287.2, 288.7, 808; 204/415; 436/536, 537, 764, 765, 172, 800, 805, 518

[56] References Cited

U.S. PATENT DOCUMENTS

| | | | |
|---|---|---|---|
| 4,626,513 | 12/1986 | Burton et al. | 436/543 |
| 4,822,733 | 4/1989 | Morrison | 435/6 |
| 4,828,981 | 5/1989 | Maggio | 435/7 |
| 4,868,103 | 9/1989 | Stavrianopoulos et al. | 435/5 |
| 5,143,066 | 9/1992 | Komives et al. | 128/634 |
| 5,246,837 | 9/1993 | Schalkowsky | 435/29 |
| 5,254,477 | 10/1993 | Walt | 436/172 |
| 5,342,789 | 8/1994 | Chick et al. | 436/501 |
| 5,439,797 | 8/1995 | Tsien et al. | 435/7.21 |
| 5,525,475 | 6/1996 | Ladouceur | 436/514 |

OTHER PUBLICATIONS

Komives et al., Talanta. 39(4):429–441, 1992.
Mansouri et al., Biotechnology. 2(1):885–890, 1984.
Meadows et al., Anal. Chim. Acta. 280(1):21–30, 1993.
Schultz et al., Biotechnology and Bioengineering, No. 9:65–71, 1979.
Weber et al., Biosensor and Bioelectronics. 7(3):193–197, 1992.

*Primary Examiner*—Christopher L. Chin
*Attorney, Agent, or Firm*—Titus & McConomy

[57] ABSTRACT

A homogenous affinity assay method, and sensor using such method, for the detection and measurement of analytes that uses an unmodified polyvalent receptor-bearing molecule and having a receptor with at least two binding sites that has an affinity for an analyte of interest, and two groups of molecules wherein one group of molecules is labeled with a molecule capable of generating a measurable response when in close proximity to a label molecule on the other group of molecules. In one embodiment, the groups of molecules also have grafted on them an analog to the analyte of interest. In the absence of the analyte of interest, members of the molecule groups are brought in close proximity to each other through affinity binding to receptor-bearing molecule. This affinity binding results in the formation of a binding complex consisting of members of the first and second groups of molecules and receptors and which results in a response between the labels on the molecules which is capable of measurement. In the presence of the analyte of interest, the binding complexes dissociate due to competitive replacement of the analog with the analyte of interest and affinity binding of the analyte of interest to at least one of the binding sites on the receptors and the labels on the molecules interact in inverse proportion the concentration of the analyte of interest. In another embodiment, the receptor is the analyte of interest and the formation of the binding complexes is a measure of the analyte of interest.

17 Claims, 2 Drawing Sheets

HOMOGENOUS AFFINITY ASSAY FOR QUANTITATIVE DRUG AND METABOLITE DETERMINATION

FIELD OF THE INVENTION

The invention relates to a method, and sensor for using such method, for detecting and measuring the presence of an analyte. More particularly, the invention relates to a homogenous affinity fluorescence assay for detecting the presence of an analyte using a novel molecular proximity principle.

DESCRIPTION OF THE PRIOR ART

A variety of assay methods have been developed to detect the presence of an analyte including potentiometery, amperometry, piezo-electric mass determination, conductivity, measurement of reaction enthalpy and fluorescence. Some of these assay methods have proven useful in detecting the presence of biological components.

A variety of methods for detecting the presence of biological components in vivo have been tried. Immunoassays typically are used to detect antigens or antibodies. Two types of immunoassays exist, heterogenous and homogenous. Heterogenous assays usually involve the immobilization of the receptor-bearing molecule, typically an antibody or ligand, on or in a structure. The receptor-bearing molecule is chosen for its specificity to the analyte of interest. Unfortunately, the immobilization of the receptor-bearing molecule may change the characteristics of the receptor-bearing molecule including its affinity for the analyte. A label, suitable for the measurement method employed, may be attached to the receptor-bearing molecule either directly or indirectly. Such methods of attachment may include covalent binding. Unfortunately, the label may also change the characteristics of the receptor-bearing molecule. Typically, a sample containing the analyte of interest is exposed to the antibody or ligand attached to the structure. When the analyte encounters the antibody or ligand, a complex typically is formed. This complex may result from affinity binding. The amount of analyte present in the sample is determined using the label.

Heterogenous assays are often performed as sandwich assays in which the analyte-receptor complex formed is almost irreversible. A molecule bearing a label and having an attraction to the analyte-receptor complex is reacted with the analyte-receptor complex. The excess label-bearing molecule is washed away and the amount of the analyte present is determined by measuring the label-analyte-receptor complexes. Unfortunately, these assays involve numerous steps, are time-consuming, and are too complex to be used in a variety of settings.

Homogeneous assays, in contrast, are performed directly. Several homogenous assays use an enzyme as a way of attaching an indicator to the receptor. However, attaching such an indicator to the receptor-bearing molecule often requires a complex chemical process. The enzyme must be a proper size and must be in a proper orientation for the attachment of the indicator. Many homogenous assays use radioactive material thereby creating health and safety issues for their use and contraindicating their use in vivo biomedical applications.

Assays are often used in contexts, in particular, biomedical applications in which it is not possible to label the analyte of interest. Accordingly, a labelled analyte analog is introduced into the system and it is possible to measure the amount of the analyte present using a competitive reaction process. In a competitive reaction process, the analyte and an analyte analog compete to bind to available receptor sites on the receptor-bearing molecule. The sample containing the analyte and analyte analog is exposed to the receptor-bearing molecule in a manner and for a sufficient period of time, such that substantially all of the available receptors are bound to either the analyte or the analyte analog. The analyte analog is labelled, and the sensor appropriate to the form of labelling is applied. The amount of the analyte present is inversely proportional to the measure of the analyte analog-receptor complex.

Other assays in the prior art that use an analyte analog to detect the presence of an analyte rely upon the analog impairing the binding of the analyte to the receptor-bearing molecule. These types of assays require that the analog be of sufficient size to impair the binding of the analyte to the receptor of the receptor-bearing molecule. This type of assay is common when the receptor is an enzyme and the analyte is a substrate. Although it is possible to design such a system, it is much more difficult to calibrate the analog such that it is of sufficient size to impair the binding of the analyte. Furthermore, the binding of a large component, whether a label or an analog, to the receptor-bearing molecule can cause drastic changes in the characteristics of the receptor-bearing molecule.

A disadvantage of most of the competitive assays used to detect biological components is that they require chemical modification of the receptor and purification of the receptors. The receptors used in most conventional biological competitive assays are antibodies or membrane proteins and the modification and purification of those antibodies is costly and inefficient. Further, the coupling of bulky dye molecules to the amino acids and/or other groups of antibodies can dramatically change the binding characteristics of those antibodies.

A variety of assays have been developed using fluorescence and the quenching and amplification of fluorescence to detect and measure the presence of the analyte of interest. With respect to fluorescence quenching as a measurement method, it is known in the art that the florescence of a fluorochrome is quenched when a dye that quenches the light emitted by the fluorochrome is about 50 angstroms or closer to the fluorochrome. These assays operate on the principle that when the dye is sufficiently close to the fluorochrome, energy emitted from the excited fluorochrome is transferred to the nearby dye which results in a measurable reduction of the amount of the net magnitude of the light that can be detected. Conventional assays that utilize fluorescence quenching as a measurement mechanism require attaching a fluorescent label or dye to the receptor-bearing molecule. Further, conventional competitive fluorescent assays require-attaching a fluorescent label or dye to the receptor-bearing molecule which interacts with the fluorescent label or dye of the polymer bearing an analog to the analyte of interest. When the analyte of interest binds with the receptor, the fluorescence of the receptor is quenched.

Several assay methods have been employed to measure glucose and galactose. Furthermore, a variety of glucose sensors are known in the prior art. Despite the advances in the prior art, a need still exists in the art for a biochemical assay that is sensitive, non-radioactive, inexpensive and easy to handle that can be used in automated biosensors.

SUMMARY OF THE INVENTION

The present invention overcomes many of the deficiencies of the assay methods used to measure the presence of an analyte described in the prior art. Applicants' method provides a new method for the measurement and detection of analytes present in biological systems. Generally, Applicants' method uses two groups of molecules, herein called P1 and P2, labelled respectively with two different types of molecules, herein called B1 and B2. In one embodiment, the receptor is the analyte of interest and an analog is not necessary. In another embodiment, P1 and P2 also have an analog to the analyte of interest grafted onto them such that the labelled and grafted molecules have an affinity for and specificity to the receptor of the receptor-bearing molecule and the labelled function as an analog to the analyte of interest. The two groups of molecules bearing the label and analog preferably are macromolecules when used in a biosensor and even more preferably the groups of molecules are polymers. P1 and P2 can be the same or of different construction. B1 and B2 are chosen based on their demonstrated ability to interact with each other when in close proximity with each other and which interaction is capable of detection and measurement. The type of label attached to the members of the molecule groups may vary depending on the detection method used, but preferably, at least one of the labelling molecules will be a fluorochrome that has an emission spectrum that overlaps with the absorption spectrum of the second label molecule, which will mask the intensity of the light emitted by the first molecule when the first and second molecule are in close proximity with the other. Preferably, the concentration of the analog P1B1 is approximately equal to the concentration of the analog P2B2. Further, preferably, the P1B1 and P2B2 are not present in the system in so great a concentration that unbound analog polymers interact to produce the same result as bound analog polymers in close proximity to each other.

The analyte analogs may be present on the molecular groups in a multiplicity of sites. Because the analyte analogs may be present on their polymers in a multiplicity of sites, the polymers can have a number of sites with which to bind to the receptor and crosslinking may occur among the receptor-bearing molecules.

Preferably, when used in a biosensor, the molecular groups bearing the analyte analogs and labels are macromolecules, preferably polymers, and even more preferably have a molecular weight that is 100 times the weight of the analyte such that they may be held in a chamber of a sensor that has a membrane that is permeable to the analyte but impermeable to them by virtue of their size. Furthermore, the tails of the molecules bearing the analog and B1 and B2 may be of sufficient length and flexibility such that they intertwine when they are in close proximity to each other.

The receptor-bearing molecule may have a multiplicity of receptor cites. Furthermore, each receptor on the receptor-bearing molecule can have any multiplicity of binding cites but must have at least two binding cites that are specific to and have an affinity for the analyte analogs and the analyte of interest. The receptor functions as a device that maintains the necessary proximity between B1 and B2 close so that they have their desired and measurable effect on each other. The receptor material is a substance from the group consisting of bioreceptors, enzymes, antibodies, nucleic acids and receptor proteins. The receptor-bearing molecule may be a variety of types but preferably is a protein. Preferably, the receptor-bearing molecule has a high affinity constant such as is found in antibodies.

When the analyte of interest is not present, a mixture of affinity crosslinked and branched structures of the receptor-bearing molecule and molecular groups bearing the labels is formed. These reactions are shown below where P1B1 is the first molecular group bearing the analyte analog and label B1, P2B2 is the second molecular group bearing the analyte analog and label B2, and R is the receptor on the receptor-bearing molecule:

When the analyte of interest is present in a system containing P1B1R, P2B2R and P1B1RP2B2, these receptor-analog-molecular group complexes dissociate due to mass action. The reactions caused by the analyte in a system containing P1B1R, P2B2R and P1B1RP2B2 are shown below where A is the analyte of interest:

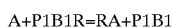

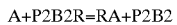

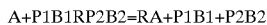

The dissociation of the receptor-analog-molecular group complexes is in proportion to the concentration of the analyte of interest. Thus, at a low analyte concentration, P1B1R, P2B2R and P1B1RP2B2 structures will persist in an inverse proportion to the concentration of the analyte. Conversely, when the concentration of the analyte has reached a receptor saturation threshold, the only crosslinked structure that will persist is the receptor-analyte structure. Thus, the degree of crosslinking between P1B1 and P2B2through attachment to R is a measure of analyte concentration and various methods for detecting the degree of crosslinking provide the basis for the new analytical method and biosensors described herein The analytical method described herein that measures the crosslinking of labelled molecules as a method of measuring the concentration of an analyte of interest, has many advantages over analytical methods described in the prior art. Many of the techniques described in the prior art rely on covalent modification of the receptor-carrying molecule for attachment of an analyte and/or analog. Covalent modification of the receptor-carrying molecule may change the properties of the receptor-carrying molecule. In contrast, the method described herein relies on affinity binding to create the crosslinking between B1 and B2 and thereby avoids the undesirable side effect of covalent modification of the receptor-bearing molecule.

Furthermore, many of the techniques described in the prior art require immobilization of the receptor-bearing molecule to employ the measurement methods. The immobilization of the receptor-bearing molecule also may change the properties of the molecule including its affinity for an analyte and/or an analyte analog.

The method described herein also has several advantages over other homogenous assays. Most other homogenous assays rely on an enzyme as a method of attaching a label to the receptor-bearing molecule. Unfortunately, the process of attaching the label to the receptor often requires a complex chemical process that requires appropriate and complex physical positioning of the receptor to the label and careful tailoring of the size of the label to ensure its effectiveness while attempting to minimize the alterations the label will have on the characteristics of the receptor-bearing molecule itself. Furthermore, many of the homogenous assays rely on a radioactive label. In contrast, the method described herein does not require the use of a radioactive label and thereby avoids the attendant health and safety problems that radioactive material imposes in any application, in particular in vivo applications.

The complexes resulting from the method described herein can have greater stability than affinity reactions described in the prior art because higher concentrations can be used. The stability of this reaction permits an extended time frame during which to detect and measure the analyte of interest and permits detection of the analyte under harsher conditions than other biologic sensor assay methods described in the prior art. The stability of the reaction resulting from the method described herein makes the method an ideal method for use in long-term monitoring of biological components.

Further, the band of analyte concentrations at which this method can be practiced is greater than that of the prior art. Additionally, because polymerization produces multiple interactions per molecule added, there is an amplification of the reaction and thus amplification of signal generated and detected by a biosensor measuring system.

It is an object of this invention to provide a method for the detection of analytes.

It is also an object of the invention to provide a method for the in vivo detection of analytes in biological systems.

It is a further object of the invention to provide for an homogenous affinity fluorescence assay for detecting the presence of an analyte using a novel competitive binding reaction.

It is an object of the invention to provide a method for quantitative drug and metabolite determination using a homogenous affinity fluorescence assay.

It is an object of the invention to provide an assay method that can be used in optical fiber sensors.

It is a further object of the invention to provide a method for measuring the amount of glucose and/or galactose in a biological system.

Other objects and advantages of the present invention will become apparent from perusing the following detailed description of presently preferred embodiments taken in conjunction with the accompanying drawings.

DESCRIPTION OF PREFERRED EMBODIMENTS

Figure 1:
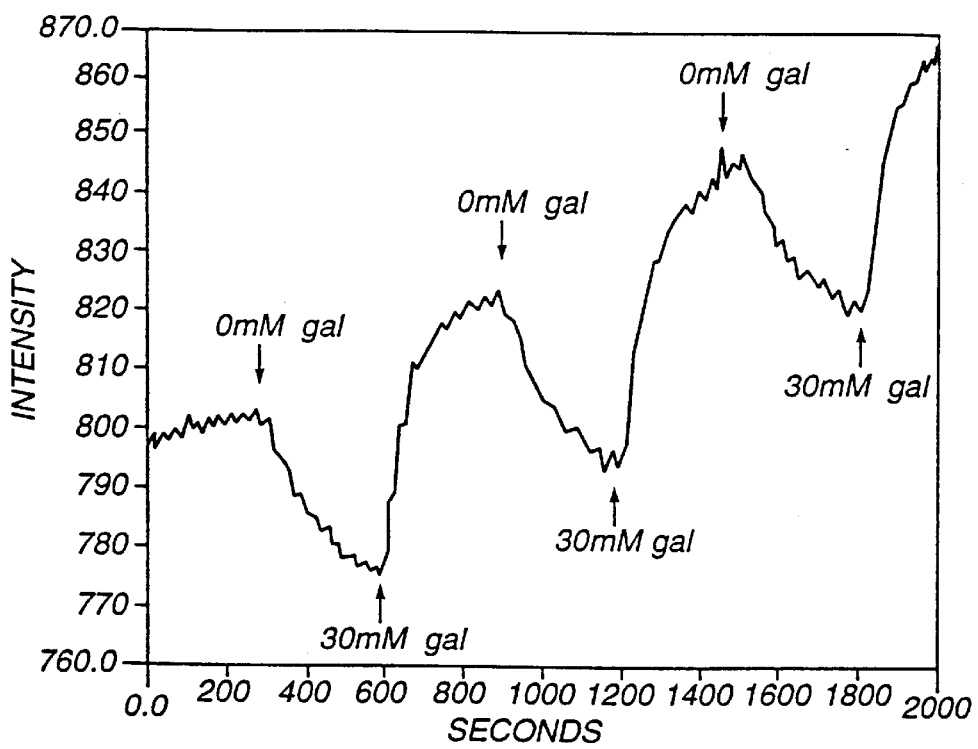
FIG. 1 reflects data generated by a system using a preferred embodiment of the invention described herein wherein the analyte of interest is galactose, the method is used in a chamber with a dialysis membrane to test the presence of galactose in an external solution, the receptor is Ricinus communis agglutinin I, the polymers are rhodamine/fluorescein labelled lactosyldextran (200 KDa, mass ratio 1:1) and the arrows indicate changes in galactose concentration.

A preferred embodiment of the method of invention described herein is the use of the method in an assay that relies on fluorescent quenching to measure the concentration of the analyte of interest. In this application of the method described herein, a first group of polymers is labeled with a biocompatible fluorochrome, herein known as B1. The labelled members of this first polymer group are herein called P1B1. The fluorochrome can be any biocompatible fluorochrome, including fluorescein. A second group of polymers, is labeled with a biocompatible dye, herein called B2, that quenches the light emitted by the fluorochrome when it is in close proximity to B1, preferably when it is within approximately 50 angstroms or less to B1. Thus, the absorption spectrum of B2 overlaps with the emission spectrum of B1. The labelled members of this second polymer group are herein called P2B2. The dye can be any biocompatible dye, including rhodamine. Further, the polymers are grafted with an analog to the analyte of interest which analog is chosen based on its affinity for and compatibility with the polyvalent receptor of the relevant receptor-bearing molecule, herein called R, and R's ability to hold the labelled polymers bearing the analog in sufficiently close proximity to each other such that B2 will be able to quench B1 when B1 and B2 are both engaged by R. Further, neither the fluorochrome B1 nor the dye B2 may substantially alter the affinity of the polymer for R.

The groups of P1B1 and P2B2 are placed in solution and introduced into the relevant system containing R which has a strong affinity for the analog and the analyte of interest, herein called A. Further, P1B1 and P2B2 are introduced into the system in concentrations below the threshold concentrations at which more than de minimis quenching would occur by virtue of B1 and B2 being extant in the system without a mechanism that would cause them to retain close proximity to each other. In the absence of A, P1B1 and P2B2 are held in close proximity to each other by R and a crosslinked structure P1B1-R-P2B2 is formed. Because of the close proximity of P1B1 and P2B2, the B2's of P2B2 excite the B1's of P1B1 and effect an energy transfer to the B2's which results in a decrease of the fluorescent light emitted by P1B1, which decrease is capable of measurement. In the presence of A, the proportion of P1B1-R-P2B2 complexes is reduced in proportion to the concentration of A. Accordingly, the amount of energy transfer between P1B1 and P2B2 is reduced and the fluorescent emission of P1B1 is increased.

The methodology described herein provides several advantages to fluorescent assay methods described in the prior art. The method described herein permits the use of an unmodified, mobile receptor. Further, the only chemical preparation required to practice the method described herein is the fluorescent labelling of the polymers bearing the analog-analyte, i.e., P1B1 and P2B2. The commercial availability of fluorescently labeled dextran, a glucose-containing hydrophilic, non-charged polysaccharide, in standardized quality and the possibility of covalently coupling a variety of ligands to the dextran makes the method described herein easy to adapt to the detection of almost any analyte.

In another preferred embodiment, the receptor is the analyte of interest and the method is used to detect the presence of the receptor. In this embodiment, the analyte is a group of molecules having a multiplicity of binding sites. P1 is a group of molecules that complement and can bind to a portion of the analyte. P1 also has a label molecule attached to at least one terminal end. P2 is a second group of molecules that complements and binds to a different but nearby portion of the analyte than that section of the analyte to which P1 is bound. P2 also has a label molecule attached to it on such a location that it interacts with the label molecule of P1 when P1 and P2 are attached to the analyte. Thus when the receptor is present, P1 and P2 are bound to it and B1 and B2 have their effect on each other which effect can be measured by a sensor. This embodiment of the method described herein can be useful when detecting and measuring the presence of nucleic acid sequences.

EXAMPLE ONE

DETECTION OF GALACTOSE

The method of invention described herein is particularly well-suited for in vivo long-term glucose and galactose monitoring when used in a continuously working biosensor device. When used in the such a device, the application of the method described herein will permit an improved method of in vivo monitoring of the concentration of glucose and galactose in biological systems thereby making clinical treatment decisions dependant on those concentrations faster, more precise and easier.

For example, galactose in the blood is extracted by the liver resulting in a steep hepatic venous-systemic venous galactose concentration gradient. A monitoring system that can detect this gradient in vivo could be used to permit cannulation of the hepatic venous system for diagnostic purposes without needing fluoroscopic assistance. Applicants present the following data as an example that demonstrates the method described herein and its suitability for in vivo biosensor application.

Applicants developed a model system that employs the method described herein in conjunction with a semipermeable hollow fiber biosensor, and demonstrates the efficacy of Applicants' method for detecting aqueous galactose in a concentration range appropriate for biosensor. In the model Applicants established to demonstrate the method described herein, the analyte of interest was galactose, the fluorescently labelled analyte analog polymers were grafted with lactosyldextran, and the polyvalent unmodified receptor was a plant lectin Ricinus communis agglutinin, also known as RCAI. The relative fluorescence characteristics of the RCAI and the lactosyldextran, the assay reagents, were studied in response to incremental increases of galactose concentrations in the range appropriate for a blood galactose sensing, more particularly, in a range appropriate for a hepatic venous sensor, i.e. a range of 0 to 1.1 mM. The galactosyldextran was enclosed in the semipermeable hollow fiber of a fiber optic probe and exposed to a flow through system that was spiked with galactose. The hollow fiber of the biosensor possessed pores large enough to permit analyte permeation but too small to permit diffusion of the receptor and polymers outside the fiber. Such hollow fiber optical probes are well-suited for the detection of biological components and the corresponding use of the method described herein because they are available in low dimensions and help ensure fast diffusion of the analyte through the biosensor system.

Although the relative fluorescence of the galactosyldextran was non-linear with respect to the galactose concentration over the range of interest, a simple mathematical formula permitted computation and measurement of the changes of galactose concentration. Applicants further tested the in vivo application of the method by introducing into the model described above physiologically relevant interfering carbohydrates such as glucose and fructose. As shown in the data depicted in FIG. 1, the model employing Applicants' method was insensitive to the additional biological components. This insensitively to extraneous common biological components, coupled with the success of the method described herein in a flow through system, demonstrate the suitability of Applicants' method for in vivo applications. Further the data shown in FIG. 1 reflect the fast kinetics of Applicants' method to the presence of the analyte. In the current example, the reaction time was approximately three to four minutes. Further, the data show good reproducibility and correlation with galactose concentration in blood. Accordingly, Applicants' method may be used in a galactose optode.

EXAMPLE TWO
DETECTION OF GLUCOSE

Figure 2:
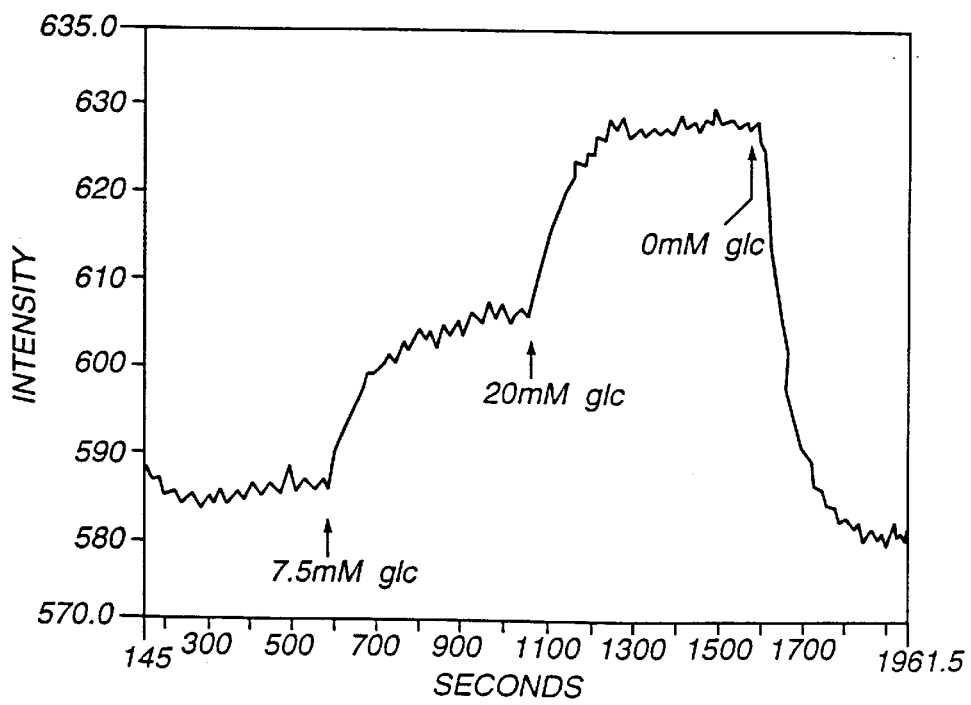
FIG. 2 reflects data generated by a system using a preferred embodiment of the invention described herein wherein the analyte of interest is glucose, the method is used in a chamber with a dialysis membrane to test the presence of glucose in an external solution, the receptor is a mannose specific lectin concanavalin A, the polymers are rhodamine/fluorescein labeled mannosyldextran (200 KDa, mass ratio 1), and the arrows indicate changes in glucose.

A mannose specific lectin concanavalin A and fluorescently labeled mannosyldextran were placed in the hollow fiber of the biosensor having the characteristics described above. The change in the fluorescence detected by the optic sensor when inserted in a solution containing glucose, again demonstrates the fast kinetics of Applicants' method (approximately three minutes) and a strong correlation to the concentration of glucose in a physiologically relevant range for blood glucose sensing (0 to 15 mM). The higher stability of Applicants' method in the optic biosensor vis-a-vis other affinity sensors based on fluorescence measurement, reflects the utility of the present invention for long-term glucose monitoring. See FIG. 2.

Examples one and two further show that one of the polymers used in Applicant's method may exist in a cross-linked form, i.e., in the form of a gel.

While presently preferred embodiments of the invention have been shown and described in particularity, the invention may be otherwise embodied within the scope of the appended claims.

What is claimed is:

1. A homogenous affinity assay method for the detection and measurement of an analyte of interest comprising:

A. Providing:
   i. an unmodified polyvalent receptor-bearing molecule having a receptor with at least two binding sites that have an affinity for the analyte of interest;
   ii. a first group of molecules grafted with an analog to the analyte of interest labeled with a first label molecule which generates a measurable response when in close proximity to a second label molecule wherein said first label molecule is attached to at least one site on each member of said first group of molecules; and
   iii. a second group of molecules grafted with said analog and labeled with said second label molecule, which said second label molecule is attached to at least one site on each member of said second group of molecules;

B. Exposing a sample suspected of containing the analyte of interest to said unmodified receptor and said first and second groups of molecules, wherein in the absence of the analyte of interest, members of said first group of molecules and members of said second group of molecules are brought in close proximity through affinity binding of said members of said first and second groups of molecules to said receptors which results in the formation of a binding complex, said binding complex consisting of said members of said first and second groups of molecules and said receptors, and which results in said response between said first label and said second label, said response being a change in the physicochemical properties of said first label molecule when it is in close proximity to said second label molecule;

wherein in the presence of the analyte of interest, said binding complexes dissociate or do not form due to competitive replacement or interaction of said analog with the analyte of interest and affinity binding of the analyte of interest to at least one said binding site on said receptors;

wherein said dissociation or said failure to form said binding complexes is in proportion to the concentration of the analyte of interest;

wherein said dissociation or said failure to form said binding complexes affects the magnitude of said response; and wherein said response is conducted in the presence of a sensor which detects and measures said response, and which sensor detects and measures said response between said members of said first and second groups of molecules;

C. Detecting and measuring said response with a sensor to determine the presence and amount of the analyte of interest.

2. A method according to claim 1, wherein said first label is a fluorochrome with an emission spectrum and said second label is a fluorochrome with a fluorescence absorption spectrum that overlaps with said emission spectrum and said response is a transfer of energy that changes the intensity of light emitted by said first label.

3. A method according to claim 1, wherein said first label is a fluorochrome with an emission spectrum and said second label is a dye with a fluorescence absorption spectrum that overlaps with said emission spectrum and said response is a transfer of energy that changes the intensity of light emitted by said first label.

4. A method according to claim 1 wherein said receptor is a lectin, an antibody, a nucleic acid or a membrane receptor.

5. A method according to claim 1, wherein said sensor has a chamber which includes a semipermeable dialysis membrane and said receptor, said members of said first and second molecule groups are placed in said chamber, wherein said dialysis membrane is permeable to the analyte of interest but is not permeable to said receptor and said members of said first and second molecule groups, and wherein said sensor measures said response between members of said first and second molecule groups in said chamber.

6. A method according to claim 1, wherein said sensor is a device which consists of a sample holder and a detector, wherein said sample holder contains a mixture of said members of said first and second group of molecules.

7. A method according to claim 1, wherein said first and second label molecules exist on a multiplicity of sites on each member of the first and second molecule groups, respectively.

8. A method according to claim 1, wherein said first label is a radioactive beta emitter and said second label is a dye with a fluorescence absorption spectrum that interacts with said beta emitter and said response is the level of radioactivity emitted by said first label.

9. An affinity sensor comprising:
A. an unmodified polyvalent receptor-bearing molecule having at least two binding sites that have an affinity for an analyte of interest, wherein said binding sites are on either one receptor or a plurality of receptors, and wherein said binding sites are in close proximity to each other;
B. a first group of polymers grafted with an analog to the analyte of interest and labeled with a first label molecule which generates a measurable response when in close proximity to a second label molecule; and
C. a second group of polymers grafted with said analog and labeled with said second label molecule;
D. a chamber having a semipermeable dialysis membrane in which said receptors, said members of said first and second polymer groups are placed, wherein said dialysis membrane is permeable to the analyte of interest but is not permeable to said receptor and said members of said first and second polymer groups;
E. a detector; and
wherein in the absence of the analyte of interest, members of said first group of polymers and members of said second group of polymers are brought in close proximity through affinity binding of said members of said first and second groups of polymers to said receptors which results in the formation of a binding complex, said binding complex consisting of said members of said first and second groups of polymers and said receptors, which affinity binding results in said response between said first label and said second label, said response being a change in the physicochemical properties of said first label molecule when it is in close proximity to said second label molecule, which said reaction is measured;

wherein in the presence of the analyte of interest, said binding complexes dissociate from said receptors due to competitive replacement of said analog with the analyte of interest and affinity binding of the analyte of interest to at least one said binding site on said receptors;

wherein said dissociation is in proportion to the concentration of the analyte of interest;

wherein said dissociation causes a change in the magnitude of said response; and wherein said detector measures said response between members of said first and second polymer groups in said chamber.

10. A sensor according to claim 9, wherein said first label is a fluorochrome with an emission spectrum and said second label is a fluorochrome or dye with an absorption spectrum that overlaps with said emission spectrum and said response is a transfer of energy that changes the intensity of light emitted by said first label which is measured.

11. A sensor according to claims 9 or 10, wherein said receptor is a lectin, an antibody, a nucleic acid or membrane receptor.

12. A homogenous affinity assay method for the detection and measurement of an analyte of interest comprising:
A. Providing:
   i. an unmodified polyvalent receptor-bearing molecule having a receptor with at least two binding sites that have an affinity for the analyte of interest;
   ii. a first group of molecules grafted with an analog to the analyte of interest labeled with a first label molecule which generates a measurable response when in close proximity to a second label molecule wherein said first label molecule is attached to at least one site on each member of said first group of molecules; and
   iii. a second group of molecules grafted with said analog and labeled with said second label molecule, which said second label molecule is attached to at least one site on each member of said second group of molecules;
B. Exposing a sample suspected of containing the analyte of interest to said unmodified receptor and said first and second groups of molecules, wherein in the absence of the analyte of interest, members of said first group of molecules and members of said second group of molecules are brought in close proximity through affinity binding of said members of said first and second groups of molecules to said receptors which results in the formation of a binding complex, said binding complex consisting of said members of said first and second groups of molecules and said receptors, and which results in said response between said first label and said second label, said response being a change in the physicochemical properties of said first label molecule when it is in close proximity to said second label molecule;

wherein in the presence of the analyte of interest, said binding complexes dissociate or do not form due to competitive replacement or interaction of said analog with the analyte of interest and affinity binding of the analyte of interest to at least one said binding site on said receptors;

wherein said dissociation or said failure to form said binding complexes is in proportion to the concentration of the analyte of interest;

wherein said dissociation or said failure to form said binding complexes affects the magnitude of said response;

wherein said response is conducted in the presence of a sensor which detects and measures said response, and which sensor detects and measures said response between said members of said first and second groups of molecules; and wherein said first label is a fluorochrome or dye with an emission spectrum and said second label is a fluorochrome or dye with a fluorescence absorption spectrum that overlaps with said emission spectrum and said response is a transfer of energy that changes the intensity of light emitted by said first label; and C. Detecting and measuring said response with a sensor to determine the presence and amount of the analyte of interest.

13. A method according to claim 12, wherein said sensor is a device having a chamber with a semipermeable dialysis membrane and said receptor, said members of said first and second molecule groups are placed in said chamber, wherein said membrane is permeable to the analyte of interest but is not permeable to said receptor and said members of said first and second molecule groups, and wherein said sensor measures said interaction between members of said first and second molecule groups in said chamber.

14. A method according to claims 12 or 13 wherein the analyte of interest is glucose and said receptor is a mannose specific lectin concanavalin A, and said members of said first group of molecules labelled with said fluorochrome are mannosyldextran.

15. A method according to claims 12 or 13 wherein the analyte of interest is galactose and said receptor is a plant lectin and said members of said first group of molecules labelled with said fluorochrome are lactosyldextrans.

16. A method according to claim 15 wherein said receptor is plant lectin Ricinus communis agglutinin, RCAI.

17. A method according to claim 12 wherein said receptor is a lectin, an antibody, a nucleic acid or a membrane receptor.

* * * * *